United States Patent [19]

Bille et al.

[11] Patent Number: 4,901,718

[45] Date of Patent: Feb. 20, 1990

[54] 3-DIMENSIONAL LASER BEAM GUIDANCE SYSTEM

[75] Inventors: Josef F. Bille, Solana Beach; Stuart I. Brown, La Jolla, both of Calif.

[73] Assignee: Intelligent Surgical Lasers, San Diego, Calif.

[21] Appl. No.: 151,569

[22] Filed: Feb. 2, 1988

[51] Int. Cl.$^4$ .......................... A61N 5/01; A61N 5/06
[52] U.S. Cl. ......................................... 60/4; 128/395; 606/18
[58] Field of Search .................. 128/303.1, 395, 362; 351/212, 241, 227

[56] References Cited

U.S. PATENT DOCUMENTS

| | | | |
|---|---|---|---|
| 4,053,845 | 10/1977 | Gould | 330/4.3 |
| 4,069,823 | 1/1978 | Isakov et al. | 128/303.1 |
| 4,091,274 | 5/1978 | Angelbeck et al. | 350/611 |
| 4,091,814 | 5/1978 | Togo | 128/303.1 |
| 4,161,436 | 7/1979 | Gould | 204/157.1 R |
| 4,210,400 | 7/1980 | Misek | 356/359 |
| 4,452,517 | 6/1984 | Kohayakawa | 351/206 |
| 4,469,098 | 9/1984 | Davi | 128/303.1 |
| 4,503,854 | 3/1985 | Jako | 128/303.1 |
| 4,517,980 | 5/1985 | Tagnon | 128/395 |
| 4,561,436 | 12/1985 | Munnerlyn | 128/303.1 |
| 4,579,430 | 4/1986 | Bille | 351/206 |
| 4,598,311 | 7/1986 | Bellina | 358/93 |
| 4,601,288 | 7/1986 | Myers | 128/303.1 |
| 4,622,967 | 11/1986 | Schachar | 128/303.15 |
| 4,638,800 | 1/1987 | Michel | 128/303.1 |
| 4,665,913 | 5/1987 | L'Esperance, Jr. | 128/303.1 |
| 4,669,466 | 6/1987 | LEsperance | 128/303.1 |
| 4,704,583 | 11/1987 | Gould | 330/4.3 |
| 4,711,542 | 12/1987 | Ichihashi et al. | 128/303.1 |
| 4,727,381 | 2/1988 | Bille et al. | 369/44 |
| 4,732,148 | 3/1988 | LEsperance, Jr. | 128/303.1 |
| 4,732,473 | 3/1988 | Bille et al. | 356/372 |
| 4,734,557 | 3/1988 | Alfille et al. | 219/121.74 |
| 4,750,486 | 6/1988 | Butler et al. | 128/303.1 |
| 4,770,172 | 9/1988 | L'Esperance, Jr. | 128/303.1 |
| 4,773,414 | 9/1988 | L'Esperance, Jr. | 128/303.1 |
| 4,784,135 | 11/1988 | Blum et al. | 128/303.1 |

OTHER PUBLICATIONS

"FM-Laser Operation of the Nd:YAG Laser," by Kuizenga et al., IEEE Journal of Quantum Electronics, Nov. 1970.

"Laser Interactions with the Cornea," by Krauss et al., Survey of Ophthalmology, Jul.-Aug. 1986.

"Configuring an Electrostatic Membrane Mirror by Least-Squares Fitting with Analytically Derived Influence Functions," Claflin et al., J. Opt. Soc. Am. A., Nov. 1986.

"3D Imaging of the Human Eye Using the Laser Tomographic Scanner LTS," by Bille et al., publication and date unknown.

"Defects in the Optical Synthesis," publication and date unknown.

Primary Examiner—Lee S. Cohen
Assistant Examiner—David Shay
Attorney, Agent, or Firm—Nydegger & Harshman

[57] ABSTRACT

A laser beam guidance system comprises a combination of mirrors that establishes an optical channel within which the laser beam is confined for movement. The system also includes means for moving the combination of mirrors to spatially reorient the optical channel. A beam steering scanner located on the path of the laser beam moves the beam within the optical channel onto selected paths which generally follow the longitudinal axis of the channel. Additionally, a focusing element in the system brings the beam into focus at selectable points on the beam. In accordance with a preestablished program, the beam is moved within the channel and focused at points along the beam to photochemically affect cells in the cornea of the eye.

3 Claims, 3 Drawing Sheets

3-DIMENSIONAL LASER BEAM GUIDANCE SYSTEM

BACKGROUND OF THE INVENTION

This invention relates generally to laser guidance systems. More particularly, this invention relates to a guidance system for focusing a laser at preselected points along preselected paths in three dimensional space. This invention is particularly, but not exclusively, useful as a guidance system for focusing a laser beam on the eye of a patient to photochemically alter selected cells in the cornea of the human eye.

DISCUSSION OF THE PRIOR ART

Within the last several years, the utility of laser beams in several unrelated fields has been widely recognized. As this recognition increases there is also greater awareness that a substantial limitation on the effective employment of laser beams is imposed by the beam's guidance system. As is well known, it is a fairly simple matter to merely aim a laser beam. It is something quite different when it is necessary to move the path of the beam and simultaneously vary its focal point on the path of the beam in order to guide the focal point along a predetermined course in three dimensional space. The present invention deals with such a guidance system and, more particularly, is concerned with guidance systems useful in fields where movement of the laser beam's focal point requires a great deal of precision.

Ophthalmic surgery is one of several fields in which precise movement and focusing of a laser beam is essential. While angiosurgery and neurosurgery, as well as numerous industrial applications, can benefit from an improved laser guidance system, ophthalmic surgery poses some unique problems. For instance, the delicate nature of the eye limits the trauma to which it can be subjected. Furthermore, what little tissue there is must be carefully worked with and, if it is good tissue, preserved whenever possible. The conclusion to be reached is that ophthalmic surgery requires as much precision as can be technically obtained.

In response to these considerations, the present invention recognizes the need for a guidance system which can sequentially aim short duration laser pulses onto separate, selected target areas of the eye at a high pulse repetition rate. More specifically, the present invention recognizes the need for a guidance system which can simultaneously steer and focus a laser beam in a controlled manner. Indeed, the present invention recognizes the need for a system which can effectively guide a laser beam like the one disclosed in U.S. Pat. No. 4,764,930 which issued to Bille et al. on Aug. 16, 1988, for an invention entitled "Multiwavelength Laser Source" which is assigned to the same assignee as the present invention.

Several laser guidance systems have been proposed for both single wavelength and multiwavelength laser beams. For example, U.S. Pat. No. 4,638,800 to Michel discloses a "Laser Beam Surgical System" which is insertable into a body passage. For a noninvasive system, U.S. Pat. No. 4,503,854 to Jako discloses a motorized laser delivery system for surgical uses. Further, U.S. Pat. No. 4,665,913 to L'Esperance Jr. discloses an x-y scanner for an ophthalmic surgery laser which operates at a preset angle relative to the eye. None of these references, however, disclose a guidance system which optically steers and focuses a laser beam in three dimensional space within a reorientable optical channel. Furthermore, none disclose a guidance system which is capable of individually focusing laser pulses at various focal points, wherein pulses in the beam are of equal intensity and equal duration and are continuously generated at an extremely high repetition rate. The present invention recognizes the need for such a guidance system in ophthalmic surgery.

In light of the above, it is an object of the present invention to provide a guidance system which optically steers the focal point of a laser beam along a predetermined course in three dimensional space. It is another object of the present invention to provide an effective guidance system for a laser beam which comprises short duration laser pulses that are delivered at a very high repetition rate. Still another object of the present invention is to provide a precision laser beam delivery system which is effective for use in ophthalmic surgery. Yet another object of the present invention is to provide a laser guidance system which is cost effective and easy to use.

SUMMARY OF THE INVENTION

A preferred embodiment of the novel guidance system for a laser beam includes a source of monochromatic light which establishes the beam. Focusing means and means for steering the beam along selected paths are provided within the system and are programmably operated in concert to bring the laser beam into focus at predetermined points in space. The system also includes a combination of mirrors which cooperate together to establish a director. While the director is held substantially stationary during laser beam transmissions, it is otherwise moveable to reorient the system onto selected areas of the eye according to the desires of the operator or in accordance with a predetermined program. Between the laser source and the eye itself, the system establishes an optical channel through which the beam is steered.

In part, the steering means comprises a fine tuner which is, perhaps, more accurately referred to as a beam steering scanner. This fine tuner has a cooperating pair of galvanometric mirrors positioned in the path of the laser beam to direct the laser beam through the optical channel along selected paths. The cooperation of these mirrors for steering the laser beam is best understood by conceptually recognizing that the first galvanometric mirror is rotatable to reflect the laser beam only along paths in a reference plane. While this first mirror is so confined, the second galvanometric mirror, depending only on the laser beam's path in the reference plane, is rotatably operable to move the laser beam in any of a series of planes which are perpendicular to the reference plane. Thus, it is a concerted effect of both galvanometric mirrors that steers the laser beam within the optical channel.

The laser beam guidance system also includes a telecentric arrangement of convex lenses which are moveable to focus the laser at a selected point on the path of the laser beam. Additionally, the system includes an active mirror which, in cooperation with the telecentric arrangement, is programmed to fine focus the laser beam and to make minor focusing adjustments which may be necessitated by nonhomogeneities of the material in the target area of the beam.

Cooperation of the various elements of the laser guidance system is coordinated by computer programming that provides appropriate inputs to the elements for operation of the system. specifically, the movement of the laser beam within the optical channel by the fine tuner and the focusing of the laser beam by the telecentric arrangement can be computer coordinated to cause the laser beam's focal point to follow a predetermined spatial path. More specifically, the focal point of the laser beam can be steered by the system during laser surgery to follow a desired path which is predetermined according to surgical requirements and the topography of the human eye.

The novel features of this invention as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
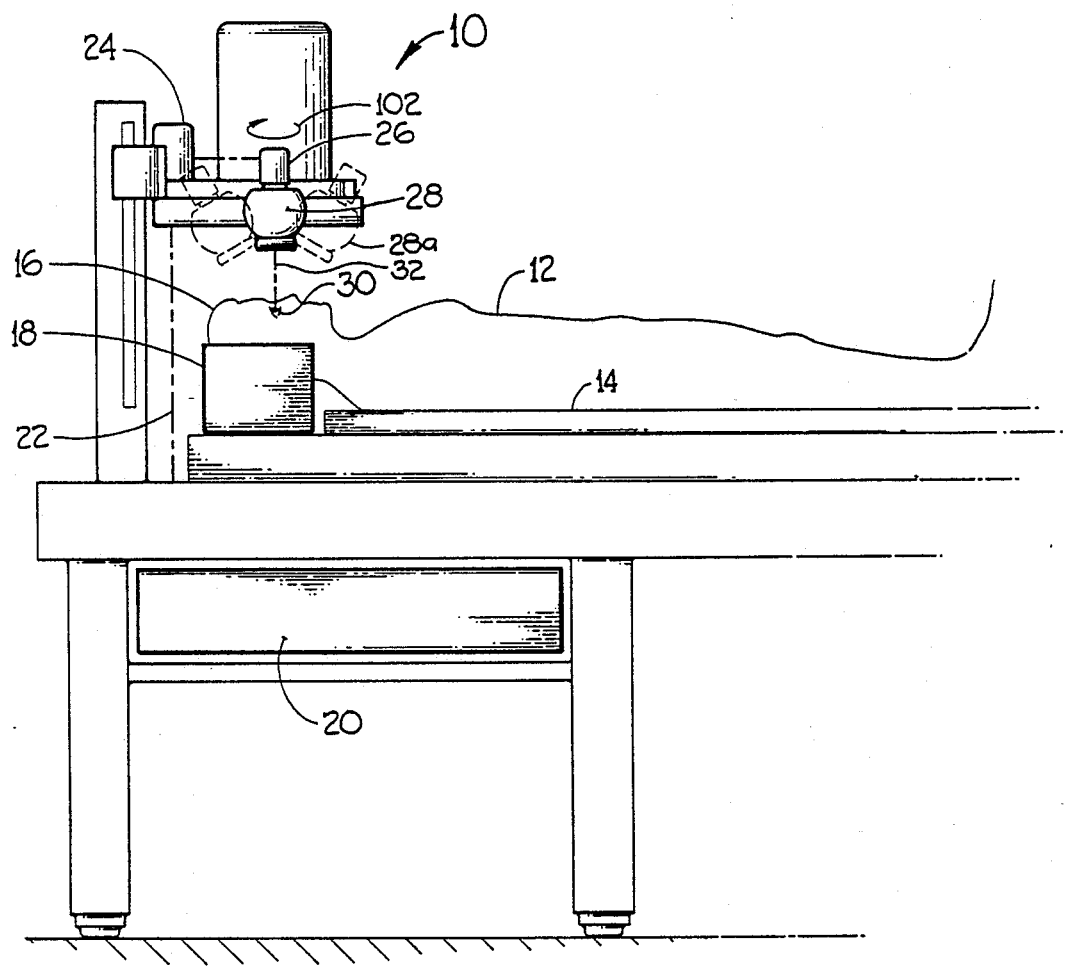
FIG. 1 is a side elevation view of the guidance system of the present invention operatively positioned for surgery on a patient's eye.

Referring initially to FIG. 1, the apparatus for the laser guidance system of the present invention, generally designated 10, is shown in operational relationship with a patient 12. As shown in FIG. 1, patient 12 is positioned on an operating table 14 with his/her head 16 placed in support 18 for a stabilized spatial relationship with apparatus 10. With patient 12 positioned in this manner, apparatus 10 may be used for its intended purpose. It will be appreciated, however, that patient 12 may also be placed in a seating posture and apparatus 10 can still be used for its intended purpose.

The major components of the laser guidance system in accordance with the present invention are best seen in FIG. 1. In FIG. 1, it is seen that a laser source 20 provides monochromatic light which is directed as a laser beam 22 along a path as substantially shown. Preferably, laser source 20 is of the type disclosed in our co-pending application for an invention entitled "Multiwavelength Laser Source" which is assigned to the same assignee as the present invention and whose disclosure is incorporated herein by reference. As shown in FIG. 1, laser beam 22 is directed through a fine tuner 24 which acts as a beam steering scanner for positioning laser beam 22 in a manner to be subsequently discussed. Upon being steered by fine tuner 24, laser beam 22 passes through a focusing element 26 and is directed from there through a position director 28 and aimed onto eye 30 of patient 12. The structure and cooperation of structure of the various components comprising apparatus 10 will be best understood by specific consideration of the individual elements of each component.

Figure 2:
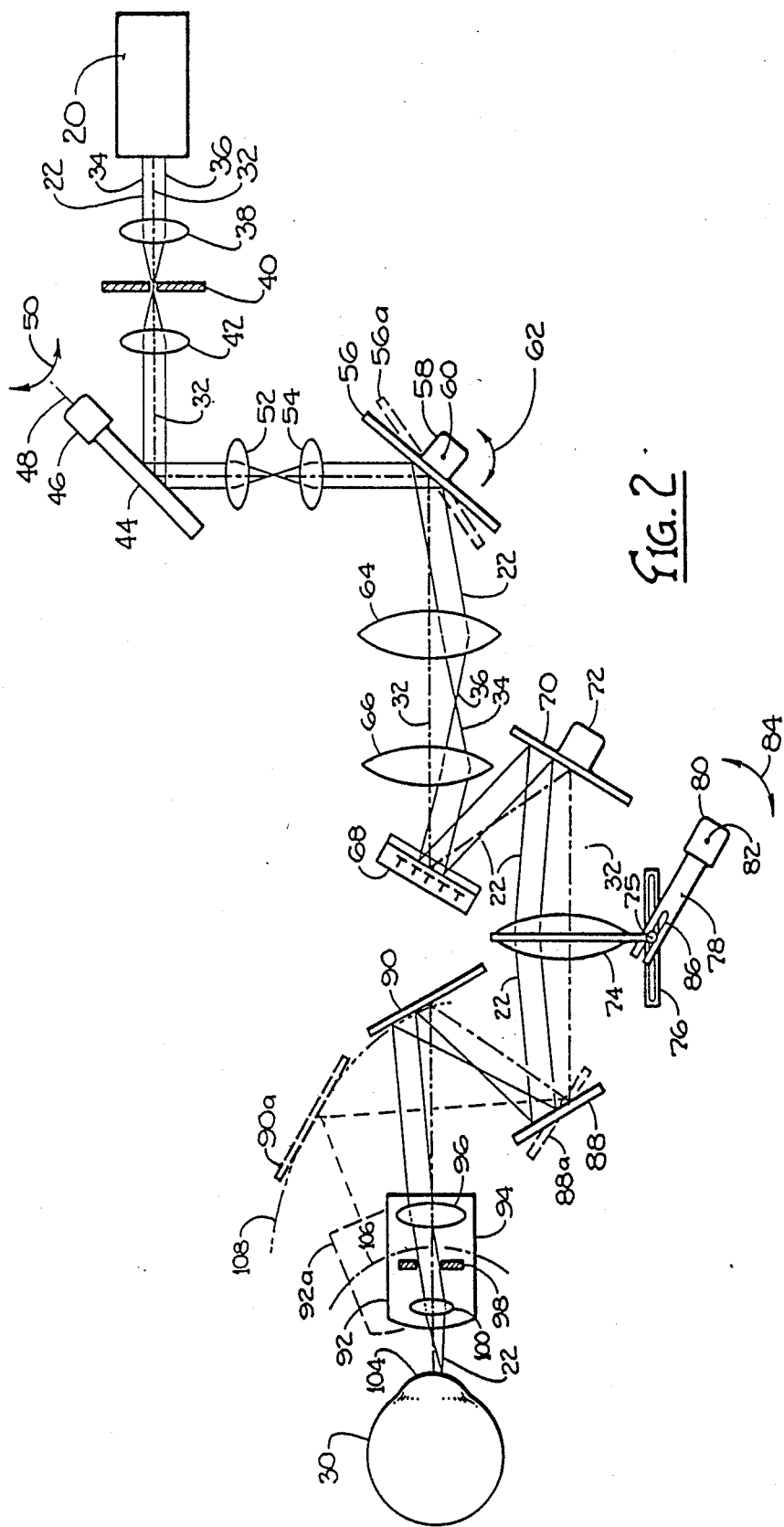
FIG. 2 is a schematic drawing of the optical elements of the guidance system shown in relationship to an eye, with portions of the system shown in phantom to represent repositioned orientations of selected optical elements.

Referring now to FIG. 2, a laser source 20 is shown establishing a laser beam 22. Upon leaving laser source 20, beam 22 generally follows an optical axis 32 completely through the system. In FIG. 2, beam 22 is representively defined by boundaries 34 and 36. As so defined, movement of laser beam 22 within apparatus 10 will effectively be confined by operational parameters of the various optical elements which are aligned along optical axis 32 of apparatus 10. Conceptually, the envelope within which movement of laser beam 22 is operably confined will be referred to herein as an optical channel. Though no reference character identifies the optical channel, it effectively extends from laser source 20 completely through apparatus 10 to the point at which laser beam 22 is focused on a target for its intended operational purpose onto the eye 30.

After leaving laser source 20, laser beam 22 is incident upon a spatial filter which comprises sequentially, along optical axis 32, a convex lens 38, an aperture 40 and a convex lens 42. As will be appreciated by the skilled artisan, this spatial filter provides a telescopic imaging system which effectively transfers collimated light to collimated light.

Next in sequence along optical axis 32, is a galvanometric mirror 44. As intended by the present invention, galvanometric mirror 44 is rotatable by galvanometer 46 about the axis 48 in the directions indicated by arrow 50. As will be more fully appreciated after subsequent disclosure, galvanometric mirror 44 is used to direct laser beam 22 off of optical axis 32. Upon being reflected by galvanometric mirror 44, laser beam 22 passes through a telescopic imaging system that comprises convex lenses 52 and 54 which are of a type well known in the pertinent art. Laser beam 22 is then incident on galvanometric mirror 56.

Like galvanometric mirror 44, galvanometric mirror 56 is used to direct laser beam 22 off of optical axis 32. Indeed, the effect of steering beam 22 within the optical channel is actually accomplished by mirrors 44 and 56 directing laser beam 22 off axis 32 in mutually perpendicular directions. Although mirrors 44 and 56 direct beam 22 in different directions, their function is the same. Accordingly, a disclosure for only mirror 56 is given.

Galvanometric mirror 56 is rotatable by galvanometer 58 about an axis 60 in the directions indicated by arrow 62. After reflection from galvanometric mirror 56, laser beam 22 passes through the telescopic imaging system comprising convex lenses 64 and 66. In FIG. 2, variation in the path of laser beam 22 off of optical axis 32 is seen as the reflected beam 22 from galvanometric mirror 56. Specifically, the rotation of galvanometric mirror 56 about the axis 60 by galvanometer 58 from a centered position 56a, will cause laser beam 22 to be reflected off of the optical axis 32 and into the position shown. Although beam 22 is directed off axis at this point, convex lenses 64 and 66 redirect laser beam 22 to its proper focal point on active mirror 68. The net effect is that the compatibility of the imaging planes is maintained, in a manner and for purposes well known, while the position of beam 22 is shifted. It is to be understood that if galvanometric mirror 56 is positioned as 56a, laser beam 22 would be colinear with optical axis 32. Further, as stated above, galvanometric mirror 44 causes a similar movement of beam 22 in a perpendicular plane.

The active mirror 68 is provided in apparatus 10 for several reasons. First, incorporation of active mirror 68 allows laser beam 22 to be finely focused to compensate for aberrations which were caused by angular scans through the cornea of a human eye in the target area. Also, this fine focusing can be made to account for cornea shapes that deviate from a perfect sphere. In sum, active mirror 68 allows for very precise focusing of the laser beam 22 in the target area. For purposes of the present invention, active mirror 68 may be of the type described in detail in the article by Claflin and Bareket entitled "Configuring an Electrostatic Membrane Mirror by Least-Squares Fitting with Analytically Derived Influence Functions" which appeared in the J.Opt.Soc.Am. Nov. 1986.

Still referring to FIG. 2, it will be appreciated that because laser beam 22 is directed off optical axis 32 in proportion to the rotational movements of galvanometric mirrors 44 and 56, it is not incident upon galvanometric turning mirror 70 on optical axis 32. Instead, as shown, laser beam 22 is incident on turning mirror 70 off optical axis 32 according to the directions imparted by galvanometric mirrors 44 and 56.

After being reflected by galvanometric turning mirror 70, laser beam 22 passes through focusing lens 74. As schematically shown in FIG. 2, focusing lens 74 is slidably attached to rail 76 for linear movement therealong. The actual position of focusing lens 74 relative to rail 76 is determined by arm 78 which moves in response to galvanometer 80. Specifically, movement of arm 78 is a rotational movement about axis 82 in the directions indicated by arrow 84. It will be appreciated that the interconnection between arm 78 and focusing lens 74 results from the sliding movement of attachment point 75 on focusing lens 74 along rail 76 and within the slot 86 shown on arm 78. Thus, in a manner well known to the skilled artisan, focusing lens 74 is moved back and forth along rail 76 to focus beam 22.

Laser beam 22 is reflected by turning mirror 88 and directed therefrom toward plane mirror 90. Plane mirror 90, in turn, directs laser beam 22 toward objective lens system 92 which is shown in FIG. 2 to be mounted within a housing 94. More specifically, objective lens system 92 comprises a convex lens 96, an aperture 98 and a convex lens 100 which cooperate, in a manner well known in the pertinent art, to bring laser beam 22 into operative focus on a selected portion of eye 30.

It is to be understood that turning mirror 88, plane mirror 90 and objective lens system 92 comprise a director which is capable of effectively reorienting the optical channel. More specifically, it will be appreciated that a rotation of turning mirror 88 from its position as shown in FIG. 2 into a position shown in phantom as 88a will reflect laser beam 22 toward plane mirror 90 when plane mirror 90 is moved into the position shown in phantom in FIG. 2 as 90a. Consequently, objective lens system 92 will need to be moved into a phantom position shown as 92a in FIG. 2. In this manner, the path of laser beam 22 can be repositioned with respect to the topography of eye 30. It is important that the movements of turning mirror 88, plane mirror 90 and objective lens system 92 be accurately coordinated. Also, it is important that proper alignment be maintained within the director. Specifically, in making the assumption that the cornea 104 of eye 30 is spherical, it follows that the path of objective lens system 92 must follow a circular path 106. It will be understood that the center of curvature for path 106 is coincident with the center of curvature of the cornea 104. The implication in movement of objective lens system 92 along circular path 106, however, is that plane mirror 90 needs to be moved along an elliptical path 108. It is to be understood that a focal point of path 108 is the point of rotation of pivoting mirror 88 and the other focal point of path 108 is the center of curvature of cornea 104. It happens that movement of plane mirror 90 along elliptical path 108 and movement of objective lens system 92 along circular path 106 maintain a proper orientation of laser beam 22 with respect to cornea 104 of eye 30. More specifically, the optical distance from the surface of convex lens 74 to the pupil 98 of the objective lens 100 can be held constant while the axis of the objective lens 100 is rotated up to 40 degrees in the transverse direction. Some nonlinearities, however, are introduced into objective lens system 92 by the movement of plane mirror 90 along elliptical path 108. Consequently, plane mirror 90 itself can be galvanometrically controlled to eliminate these nonlinearities. Alternatively, it is necessary that feedback signals representing these nonlinearities be used to turn galvanometric turning mirror 70 in a manner which will compensate for the nonlinearities.

Figure 3:
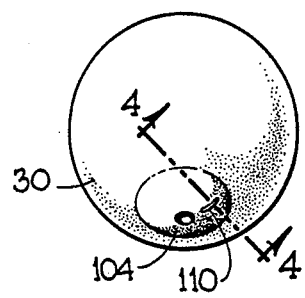
FIG. 3 is a perspective view of an eye.

From FIG. 2, it will be understood by the skilled artisan that movement of objective lens system 92 into the phantom position 92a repositions laser beam 22 relative to cornea 104 of eye 30 along an arc on the surface of cornea 104. It happens that for full utilization of the present invention, objective lens system 92 must also be capable of rotating about the optical axis 32 in a manner which would describe a circular path on the surface of cornea 104 as shown in FIG. 3. Reference to FIG. 1 shows this operation can be easily accomplished if the rotational axis of objective lens system 92 is co-linear with that portion of optical axis 32 which is established between active mirror 68 and galvanometric mirror 56. More specifically, referring to FIG. 1, it is to be appreciated that movement of director 28 into position 28a concurrently moves lens system 92 into its position 92a. Subsequently, movement of director 28 about axis 32 in directions indicated by arrow 102 will track circular paths on cornea 104.

Figure 4:
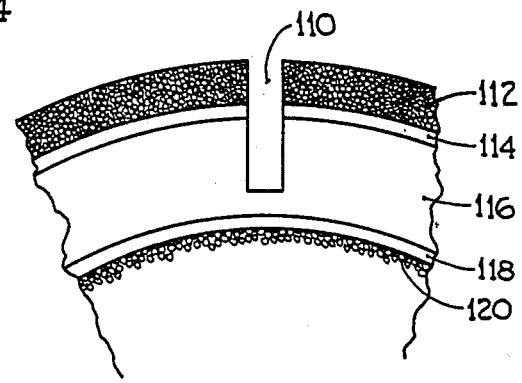
FIG. 4 is a cross sectional view of the cornea of the eye as seen along the line 4—4 in FIG. 3.

Turning now to FIG. 3, a perspective view of human eye 102 and its cornea 104 is shown with an incision 110 such as would be made into the cornea 104 during a procedure known as radial keratotomy. More specifically, as shown in FIG. 3, incision 110 is made radially on cornea 104 and in cross reference to FIG. 4 is preferably made into cornea 104 in a controlled manner. Specifically, in accordance with acceptable procedures, incision 110 should penetrate epithelium 112, Bowman's membrane 114 and only partially extend into the stroma 116 of cornea 104. Such an incision 110, however, should not compromise either Descemet's membrane 118 or endothelium 120. As would be expected by the skilled opthalmologist, an incision 110 which compromises Decimet's membrane 118 and endothelium 120 could have catastrophic consequences. Thus, it can be appreciated that the precise guidance of the focal point of a laser beam 22 in its incidence upon the cornea 104 of eye 102 is a very precise and demanding procedure. Accordingly, the present invention has elements which allow for a very precise focusing of laser beam 22 along a predetermined spatial path. Further, by cross referencing FIG. 3 and FIG. 4, it will be appreciated that the incision 110 which is to be made into cornea 104 of eye 102, must be precisely controlled in all three dimensions. Specifically, control is required in a surface orientation with respect to the surface of eye 102 and in a depth orientation with regard to the penetration of incision 110 into the cornea 104 of eye 102.

OPERATION

Figure 5:
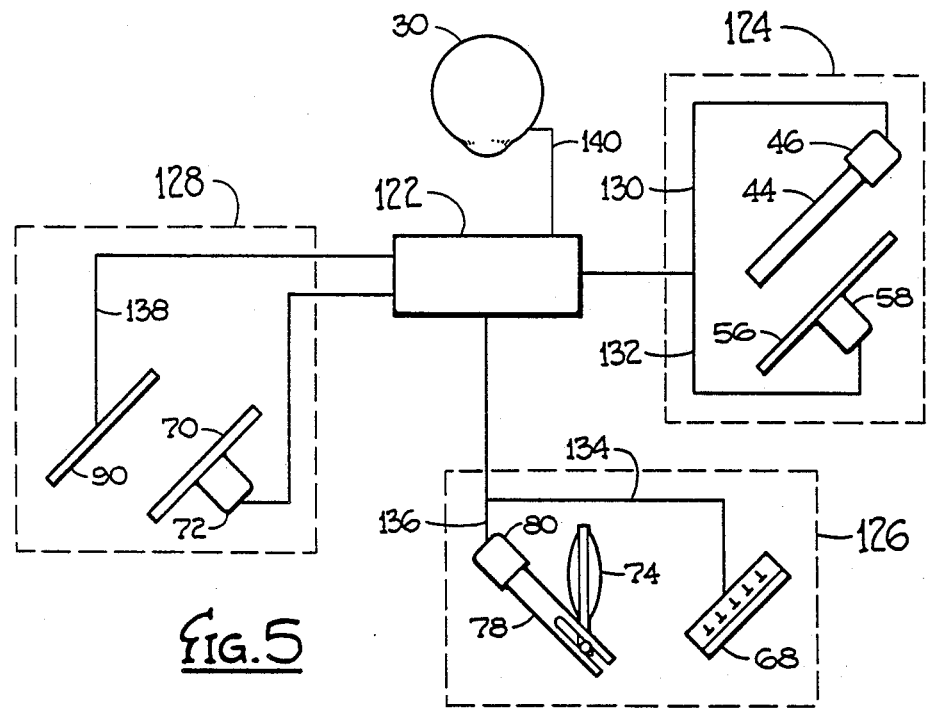
FIG. 5 is a block diagram of the connections for the electronic components of the present invention.

Operation of the apparatus 10 of the present invention will be best appreciated by reference to FIG. 5 in which a schematic block diagram of the electronic componentry of the present invention is shown. It is to be understood that, whereas FIG. 2 illustrates the optical cooperation of elements in apparatus 10, FIG. 5 is intended to show the electronic cooperation of these elements. Accordingly, not all optical components are shown in FIG. 5. On the other hand, general characterizations of the operative groups of optical elements are used. More specifically, a computer or microprocessor 122 is programmed in accordance with the desires of the operator to cause the guidance system of apparatus 10 to follow predetermined contours of eye 102. This cooperation is conceptually shown in FIG. 5 as a programmed input 140 from eye 30 to microprocessor 122. As seen in FIG. 5, microprocessor 122 is electronically connected to a beam steering scanner 124, a focusing element 126 and a position director 128 for the operation of the present invention. Reference to previous disclosure and to FIG. 5 will indicate that scanner 124 essentially comprises galvanometric mirrors 44 and 56 along with other associated components. Further, focusing element 126 essentially comprises active mirror 68 and focusing lens 74 while position director 128 comprises turning mirror 88 and plane mirror 90.

The electronic connection of microprocessor 122 with beam steering scanner 124 requires that an electrical connector 130 be connected with galvanometer 46 in a manner which will cause galvanometer 46 to rotate galvanometric mirror 44 in accordance with preprogrammed instructions from microprocessor 122. Likewise, microprocessor 122 is electrically connected to galvanometer 58 by electrical connector 132 to cause movement of galvanometric mirror 56 in accordance with preprogrammed input from microprocessor 122. It can be appreciated from the above that programmed input to both galvanometric mirrors 44 and 56 can be accomplished in a manner which will cause the steering of laser beam 22 through the optical channel of apparatus 10.

The actual steering of laser beam 22 within the optical channel is accomplished by the concerted action of galvanometric mirrors 44 and 56. As briefly stated above, it is helpful in understanding this operation to consider the actions of galvanometric mirrors 44 and 56 in isolation. Thus, for discussion purposes only, first consider galvanometric mirror 56. If galvanometric mirror 56 is centered into the position 56a shown in FIG. 3, laser beam 22 will radiate from galvanometric mirror 56 along optical path 32. However, if galvanometric mirror 56 is rotated about axis 60 into its position, as shown, laser beam 22 will be reflected off optical axis 32 in the manner illustrated in FIG. 2. Thus, it will be understood that movement of galvanometric mirror 56, without a variation or movement of any other optical element, causes laser beam 22 to move within a reference plane. Galvanometric mirror 44 has exactly the same effect on laser beam 22 in planes perpendicular to this reference plane. Accordingly, concerted action of galvanometric mirrors 44 and 56 in response to programmed signals from microprocessor 122 will steer laser beam 22. With this steerability, the remaining third dimensional control is accomplished by properly focusing laser beam 22.

The focusing element 126 of apparatus 10 is also electronically connected to microprocessor 122. Specifically, this connection requires an electrical connector 134 between microprocessor 122 and active mirror 68. Additionally, electrical connector 136 connects microprocessor 122 with galvanometer 80 for movement of pivot arm 78 in a preprogrammed manner to cause focusing of focusing element 126 in a manner well known in the art. Thus, preprogrammed input to microprocessor 122 causes focusing element 126 to focus laser beam 22 at a focal point to be determined by the operator in accordance with the particular topography of eye 102.

FIG. 5 also shows that microprocessor 122 electronically controls position director 128. Specifically, mirror 90 may be galvanometrically controlled and, consequently, no feedback linkage between mirror 90 and mirror 70 is required. Recall that in an alternate embodiment, plane mirror 90 of position director 128 can be electrically connected via connector 138 with microprocessor 122 to indicate the position of mirror 90 on elliptical path 108. This positional information is passed by electrical connector 140 from microprocessor 122 to galvanometer 72 for the purpose of moving galvanometric mirror 70 in accordance with a preprogrammed relationship with plane mirror 90. As mentioned previously, this electrical connection between plane mirror 90 and galvanometric mirror 70 is established for the purpose of correcting mechanical nonlinearities caused by movement of plane mirror 90 along elliptical path 108 in cooperation through mechanical linkage with the rotation of turning mirror 88.

In accordance with the above disclosure for the operation of apparatus 10, it will be appreciated that preprogrammed computer input to each of the various components, i.e. beam steering scanner 124, focusing element 126 and position director 128, allows apparatus 10 to accurately establish the direction from which laser beam 22 is incident upon eye 102. Thus, the location of an incision 110 into cornea 104 of eye 102 can be controlled with great accuracy. Further, computer input also precisely controls the focal point for laser beam 22 and, consequently controls the depth to which an incision 110 is to be made into cornea 104 of eye 102. The connection of the various novel elements with eye 102 is established by programmed input 140 concerning the spatial relationship between eye 102 and apparatus 10 as well as topographical and compositional information concerning eye 102.

While the particular three-dimensional laser guidance system as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An apparatus for steering and focusing a laser beam to a predetermined point in space according to the topography of an eye which comprises:
    a laser beam source having means to direct said beam along a path in an optical channel defined by an envelope in which said path of said beam is steered;
    an optical element positioned in said path to focus said beam at a preselected point on said path;
    a director positioned within said optical channel constituting means for selectively reorienting said channel in accordance with the topography of the eye, said director having a turning mirror, a plane mirror, and an objective lens system sequentially oriented in said path of said beam and moveable with respect thereto constituting means for reorienting said optical channel while maintaining the length of said optical channel; and a tuner positioned within said optical channel to receive said beam and selectively alter said path to bring said preselected point on said path into coincidence with said predetermined point in space, said tuner having a plurality of galvanometric mirrors positioned in said path of said beam to alter said path, and said optical element comprises a convex lens positionable in said path of said beam.

2. An apparatus for focusing a laser beam onto a point in a solid body having a definable external surface which comprises:

means for defining an optical channel;

means mounted on said apparatus for directing said beam through said channel and onto a first portion of said surface along a first axis substantially perpendicular to said first portion;

means mounted on said apparatus for selectively redirecting said beam through said channel onto a second portion of said surface along a second axis substantially perpendicular to said second portion, said redirecting means having a plurality of moveable galvanometric mirrors;

means mounted on said apparatus for focusing said beam along said respective first or second axis, said focusing means having a convex lens positioned in said path of said beam and moveable therealong for focusing said beam; and means for reorienting said channel with respect to said body, said reorienting means having sequentially placed in said path of said beam a turning mirror, a plane mirror, and an objective lens each moveable with respect to one another for reorienting a portion of said optical channel.

3. A method for focusing a laser beam at a predetermined point in space according to the topography of an eye which comprises the steps of:

(A) Directing a laser beam along a path;

(B) Confining said path within an optical channel;

(C) Focusing said laser beam at a preselected point on said path;

(D) Steering said path of said beam within said channel to bring said preselected point on said path into coincidence with said predetermined point in space; and (E) Reorienting said channel with a mirror according to the topography of the eye.

* * * * *